United States Patent [19]
Chan

[11] Patent Number: 5,234,002
[45] Date of Patent: Aug. 10, 1993

[54] CATHETER EXCHANGE SYSTEM

[75] Inventor: Randy S. Chan, San Jose, Calif.

[73] Assignee: Advanced Cardiovascular Systems, Inc., Santa Clara, Calif.

[21] Appl. No.: 775,281

[22] Filed: Oct. 11, 1991

[51] Int. Cl.[5] .............................................. A61B 5/00
[52] U.S. Cl. .................................................. 128/772
[58] Field of Search ............... 128/657, 772; 604/95, 604/164, 283

[56] References Cited

U.S. PATENT DOCUMENTS

| | | | |
|---|---|---|---|
| 4,726,369 | 2/1988 | Mar | 128/657 |
| 4,778,447 | 10/1988 | Velde et al. | 604/283 |
| 4,827,941 | 5/1989 | Taylor et al. | 128/772 |
| 4,875,489 | 10/1989 | Messner et al. | 128/772 |
| 5,109,867 | 5/1992 | Twyford | 128/657 |
| 5,117,838 | 6/1992 | Palmer et al. | 128/657 |

Primary Examiner—Max Hindenburg
Attorney, Agent, or Firm—Crosby, Heafey, Roach & May

[57] ABSTRACT

A connecting system for making a threaded connection between the proximal end of a guidewire having male threads and the tubular distal end of an extension wire having female threads within the tubular distal end. The female threads are preferably formed by pressing the wall of the tubular member against a threaded mandrel disposed within the inner lumen of the tubular member so that the inwardly projecting surfaces of the dimples formed are deformed against the threaded mandrel.

4 Claims, 1 Drawing Sheet

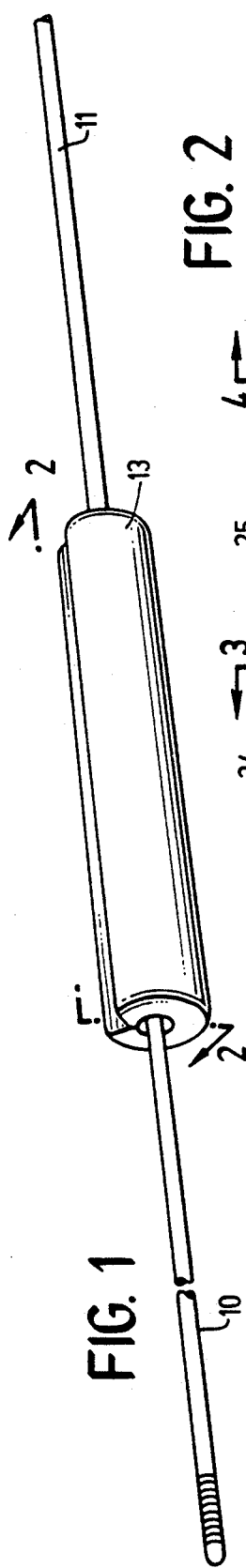
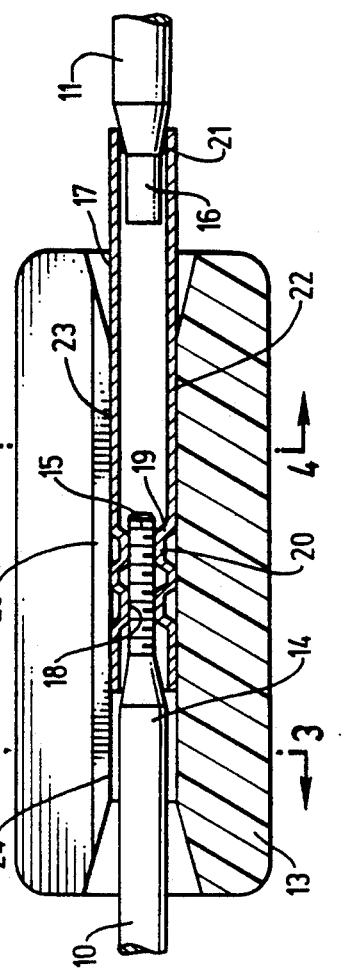
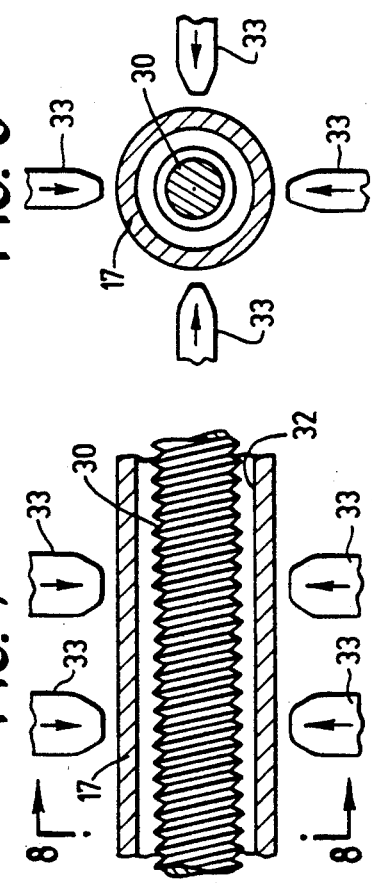
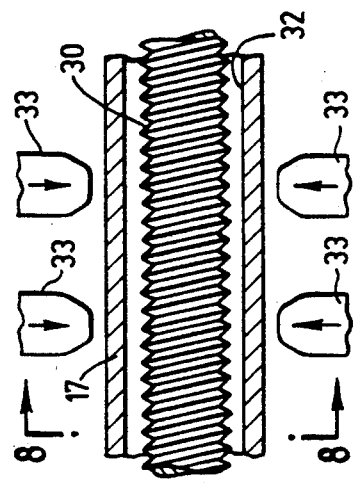
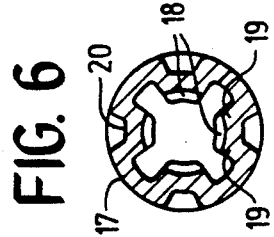
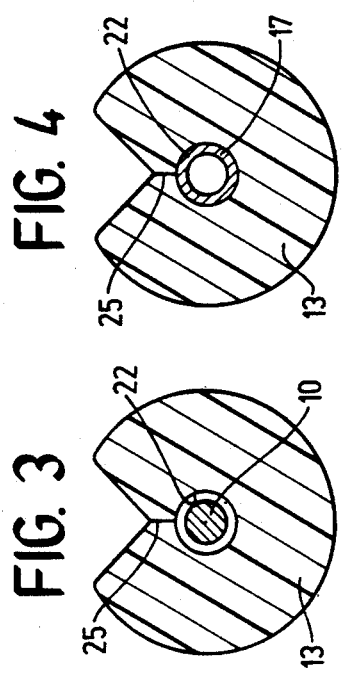
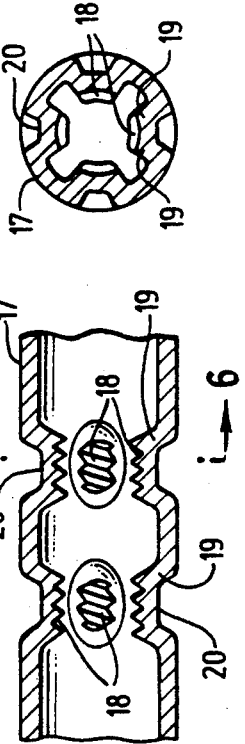

CATHETER EXCHANGE SYSTEM

BACKGROUND OF THE INVENTION

This invention generally relates to the exchange of dilatation catheters by means of an extension wire in procedures such as percutaneous transluminal coronary angioplasty (PTCA).

In PTCA procedures with over-the-wire balloon dilatation catheters, a guiding catheter having a preshaped distal tip is percutaneously introduced into the cardiovascular system of a patient and advanced therein until the preshaped distal tip thereof is disposed within the aorta adjacent the ostium of the desired coronary artery. The guiding catheter is twisted or torqued from its proximal end, which extends outside of the patient, to turn the distal tip of the guiding catheter so that it can be guided into the coronary ostium and seated therein. A dilatation catheter having an inflatable member on the distal end thereof and a guidewire slidably disposed within an inner lumen of the dilatation catheter are introduced into and advanced through the proximal end of the guiding catheter to the distal tip of the guiding catheter seated within the coronary ostium. The distal tip of the guidewire is usually manually shaped (e.g. curved) by the physician or one of the attendants before it is introduced into the guiding catheter along with the dilatation catheter.

The shaped distal tip of the guidewire is first advanced out the distal tip of the guiding catheter into the patient's coronary artery. Torque is applied to the proximal end of the guidewire, which extends out of the proximal end of the guiding catheter, as the guidewire is advanced within the coronary anatomy, to guide the curved or otherwise shaped distal end of the guidewire into the desired branch artery targeted for dilatation. The advancement of the guidewire within the target artery continues until it crosses the lesion to be dilated.

The balloon dilatation catheter is then advanced out of the distal tip of the guiding catheter, over the previously advanced guidewire, until the balloon on the distal extremity of the dilatation catheter is properly positioned across the lesion to be dilated. Once properly positioned across the lesion, the flexible, relatively inelastic dilatation balloon on the catheter is inflated to a predetermined size with radiopaque liquid at relatively high pressures (e.g., generally 4-12 atmospheres) to dilate the stenosed region of the diseased artery. One or more inflations of the balloon may be required to complete the dilation. After the last dilation, the balloon is deflated so that the dilatation catheter can be removed from the dilated stenosis and so that blood flow can resume through the dilated artery.

Further details of guiding catheters, dilatation catheters, guidewires, and the like for angioplasty procedures can be found in U.S. Pat. No. 4,323,071 (Simpson-Robert); U.S. Pat. No. 4,439,185 (Lundquist); U.S. Pat. No. 4,468,224 (Enzmann et al.); U.S. Pat. No. 4,516,972 (Samson); U.S. Pat. No. 4,438,622 (Samson et al.); U.S. Pat. No. 4,554,929 (Samson et al.); U.S. Pat. No. 4,582,185 (Samson); U.S. Pat. No. 4,616,652 (Simpson); U.S. Pat. No. 4,638,805 (Powell); U.S. Pat. No. 4,748,986 (Morrison et al.); U.S. Pat. No. 4,898,577 (Badger et al.); U.S. Pat. No. 4,748,982 (Horzewski et al.); U.S. Pat. No. 4,821,722 (Miller et al.); U.S. Pat. No. 4,827,943 (Taylor et al.); U.S. Pat. No. 4,898,577 (Badger et al.); U.S. Pat. No. 4,966,163 (Kraus et al.); and U.S. Pat. No. 4,998,923 (Samson et al.) which are incorporated herein in their entirety by reference thereto.

It is not uncommon during an angioplasty procedure for the dilatation catheter to be exchanged. While there are a variety of reasons for such catheter exchanges, it is usually done to provide a dilatation catheter with a more appropriately sized balloon. To effect the catheter exchange, typically an elongated extension wire is secured to the proximal end of the guidewire which extends out of the patient. The length of the guidewire and the extension wire which extends out of the patient must be longer than the length of the dilatation catheter to facilitate the catheter exchange without the loss of guidewire position within the patient's artery. The dilatation catheter is withdrawn from the patient over the guidewire and the extension wire until the distal end of the dilatation catheter exits the proximal end of the guiding catheter which extends out of the patient. The exposed portion of the guidewire which extends out of the guiding catheter but which is distal to the distal end of the withdrawn dilatation catheter may then be held manually so as to retain the position of the guidewire within the patient's vasculature while the dilatation catheter is completely removed from the guidewire and the extension wire.

A replacement dilatation catheter or other type catheter is then mounted onto the proximal or free end or the extension wire and advanced over the extension wire and over the guidewire connected thereto to a desired location within the patient's vasculature where additional intravascular procedures may be performed. The extension wire is usually removed, if possible, before proceeding with the additional intravascular procedure.

The aforementioned Taylor et al. patent discloses a connection of the proximal end of a guidewire to the distal end of an extension wire wherein the proximal end of the guidewire has an undulating member which frictionally engages a tubular member on the distal end of the extension wire. While this connection has been well received by the medical profession, occasionally the connection would fail and disrupt the angioplasty procedure. The Kraus et al. patent describes a system for exchanging a dilatation catheter over an extension wire wherein the proximal end of the guidewire, which extends out of the patient, is secured by a threaded connection to the distal end of an extension wire. While this system has also been well received by the medical profession, its use has been limited to angioplasty procedures in peripheral arteries due to its relatively large size. Threaded connections dimensioned for coronary angioplasty use could not be readily made by conventional methods because there is presently no convenient way of making female threads within a tubular member with an internal diameter less than about 0.02 inch, which is of the size needed for coronary angioplasty.

What has been needed and heretofore unavailable is a threaded connection system which is small enough to be used to connect an extension wire to a guidewire dimensioned for coronary angioplasty and which soundly connects the two components. The present invention satisfies this and other needs.

SUMMARY OF THE INVENTION

The present invention is directed to an improved threaded connection system which is suitable for use in connecting extension wires and guidewires and to the making of the components for the threaded connection.

The threaded connection of the invention comprises a tubular member which has internal female threads and which is adapted to receive the end of another elongated member having male threads thereon which match the female threads in the tubular member. To facilitate the joining of the threaded members, a short flexible connecting element is provided which has an inner lumen with a distal portion adapted to frictionally engage the tubular member with the female threads and a proximal portion which has a diameter or is otherwise adapted to allow the end of the elongated member having male threads thereon to freely rotate therein.

To make the threaded connection, the tubular member with female threads is inserted into the inner lumen of the connecting element through the proximal end thereof, the friction fit therebetween being sufficient to firmly secure it within the inner lumen. The distal end of the connecting element is slidably mounted over the end of the elongated member having male threads until the threaded tip engages the open end of the tubular member with the female threads. By holding the elongated member with one hand and the connecting element in the other hand with the tubular member firmly secured within the inner lumen of the connecting element, an operator can twist the connecting element so that the tubular member with the female threads wire is threadably connected to the end of the elongated member with the male threads. Preferably, the elongated member with male threads is provided with a flag or other indicia to indicate the rotation of the elongated member. When the tubular member is threaded over the end of the elongated member, complete engagement of the male and female threads is indicated when the elongated member rotates. Preferably a flag or other indicia is provided to elongated member to easily see when it rotates.

To facilitate the removal of the flexible connecting element from the connected components after the connection is made, the connecting element is preferably provided with a slit along the entire length thereof which extends through the wall of the element from the exterior thereof to the inner lumen. The slit allows the connecting element to be easily separated from the connected components by peeling the connecting element off of these components after the connection is made. The connected components may be pulled through the slit in the connecting element while the connecting element is being held to effect the separation.

The connection system is particularly useful in connecting a guidewire and an extension wire to facilitate the exchange of intravascular catheters such as dilatation catheters during angioplasty procedures. In a presently preferred embodiment, the extension wire is provided with a tubular distal end with female threads. These female threads are made by dimpling the wall of the tubular distal end with a threaded mandrel disposed within the inner lumen of the tubular distal end. The dimpled inner surface of the tubular distal end is deformed against the threaded mandrel, taking on the imprint of the threads on the mandrel. The imprinted female threads are accurate and they effectively grip the male threads on the proximal end of the guidewire. Female threads can be made in a tubular element with an ID as small as 0.005 inch or smaller in accordance with the invention.

These and other advantages of the invention will become more apparent from the following detailed description of the invention, when taken in conjunction with the accompanying exemplary drawings.

BRIEF DESCRIPTION OF THE DRAWINGS

FIG. 1 is an perspective view of a connection between a guidewire and an extension wire embodying features of the invention.

FIG. 2 is a an enlarged, longitudinal cross-sectional view of the connecting element shown in FIG. 1 taken along the lines 2—2.

FIG. 3 is a transverse cross-sectional view of the connecting element shown in FIG. 2 taken along the lines 3—3.

FIG. 4 is a transverse cross-sectional view of the connecting element shown in FIG. 2 taken along the lines 4—4.

FIG. 5 is a longitudinal cross-sectional view of the distal tubular end of the extension wire shown in FIG. 1.

FIG. 6 is transverse cross-sectional view of the distal tubular end of the extension wire shown in FIG. 5 taken along the lines 6—6.

FIG. 7 is a longitudinal cross-sectional view schematically illustrating the dimpling of the tubular member about a threaded to mandrel to form the internal female threads.

FIG. 8 is a transverse cross-sectional view schematically illustrating the dimpling of the tubular member as shown in FIG. 7 taken along the lines 8—8.

DETAILED DESCRIPTION OF THE INVENTION

FIG. 1 illustrates the overall arrangement of a connection between a guidewire 10 and an extension wire 11 with a connecting element 13 which facilitates the connection.

The details of the ends of the guidewire 10 and the extension wire 11 are shown in FIG. 2. The proximal end 14 of the guidewire 10 is provided with male threads 15 on the exterior thereof. The distal end 16 of the extension wire 11 has a tubular member 17 with internal female threads 18 which are formed on the inner projecting surface 19 of the dimpled wall 20. As shown, the tubular member 17 is a separate member which is joined to the distal end of the extension wire by welding at location 21.

FIGS. 3 and 4 illustrate a transverse cross-sectional view of the connecting element 13 and the guidewire 10 and the extension wire 11 as shown in FIG. 2.

As shown in FIGS. 2-4 the connecting element 13 has a generally cylindrical shape with an inner lumen 22 extending longitudinally therethrough. The proximal portion 23 of the inner lumen 22 is adapted to frictionally engage and secure the distal end of the extension wire 11 so that rotation of the connecting element causes the rotation of the extension wire. The distal portion 24 of the inner lumen 22 is adapted to slidably receive the proximal end of the guidewire 10. Rotation of the connecting element 13 causes the rotation of the extension wire 11 and the tubular member 17, but not the guidewire 10, and it effects the threaded connection between the ends of the guidewire and the extension wire. A flag (not shown) or other indicia may be provided to the proximal end of the guidewire distally to the male threads thereon so that upon completion of the threaded connection and the rotation of the guidewire which results, this rotation can be readily ascertained by the operator. Upon completion of the threaded connection, the connecting element 13 may be peeled off of the connected guidewire 10 and extension wire 11 through the slit 25 provided through the wall of the connecting element. The connecting element 13 is preferably formed of relatively flexible plastic material such a silicon rubber having a durometer hardness of about 45 to about 55.

After the connection is made, the dilatation catheter may be removed and replaced with another catheter in a conventional fashion as described in the BACKGROUND OF THE INVENTION. The in-place dilatation catheter is withdrawn over the guidewire 10 and the extension wire 11 until the distal end of the dilatation catheter exits the proximal end of the guiding catheter. The exposed portion of the guidewire 10 extending out of the guiding catheter (not shown) but distal to the distal end of the dilatation catheter may be manually gripped to maintain the position of the guidewire within the patient's vasculature. The proximal end of extension wire 11 is inserted into the guidewire port in the distal end of the replacement catheter and advanced therein until the proximal end of the extension wire exits the proximal end of the replacement catheter. The replacement catheter may then be advanced over the extension wire 11 and the guidewire 10 into and through the vasculature of the patient to a desired arterial location. After insertion of the replacement catheter, the extension wire 11 can be remove by twisting it to disengage the threaded connection between it and the guidewire 10.

The overall lengths, diameters and other dimensions of the guidewire 10 and the extension wire 11 will generally follow the dimensions of prior guidewires and extension wires such as those described in the TAYLOR ET AL. patent which has been incorporated by reference. It is generally contemplated that the guidewire and extension wire will be formed of conventional materials. For example, the shafts of the guidewire and the extension wire may be formed of stainless steel, tungsten or NiTi alloys, particularly those with superelastic properties at body temperatures. The tubular member 13 may be formed of stainless steel. It may be a separate element which is secured to the extension wire or the extension wire may be formed of hypotubing with the distal end being a tubular portion thereof.

Typical dimensions for the portion of the guidewire forming the connection include a guidewire shaft OD of 0.01 inch along most of the shaft which tapers to the proximal section with an OD of 0.0066 inch and a length of about 6-10 mm. The last 2-5 mm are provided with threads at about 200 threads per inch, e.g. about 25 to 30 threads. The extension wire generally has an elongated shaft with an OD of about 0.011 inch which tapers to a tip with an OD of about 0.007 inch which is adapted to fit into the tubular member 17. The tubular member 17 is formed of hypotubing with an OD of about 0.012-0.017 inch, and ID of about 0.007-0.008 inch and a length of about 2-5 cm. Four sets of two dimples are equally spaced about the circumference of the tubular member and they are spaced longitudinally about 4 to about 8 mm from the distal end of the tubular member. The two dimples of a set are spaced longitudinally about 1 mm from each other.

FIGS. 6 and 7 illustrate the formation of the dimples 20 with female threads 18 on the inwardly projection surface 19 thereof. Mandrel 30 with a threaded exterior 31 is inserted into the inner lumen 32 which extends within the tubular member 17. Four dimpling teeth 33 of a crimping tool (not shown) are pressed against the exterior surface of the tubular member 17. The inwardly projecting surface 19 of the dimples 20 formed are plastically deformed against the exterior of the threaded mandrel 30 to form female threads 18. Suitable crimping tools for forming the dimples 20 include Miniature Microcrimp Tools, Models 612118 and 620841, which are sold by Astro Tool Corporation of Beaverton, Oreg. Model 620841 is essentially the same as Model 612118 except that the crimping teeth are smaller.

The present invention has been described herein primarily in terms of guidewires and extension wires which are suitable for coronary angioplasty. However, the connection and the method for making the connection components can be applied to a wide variety of uses. For example, the connection of the invention can also be made between the proximal end of a fixed-wire dilatation catheter and an extension wire in the same manner as describe herein between a guidewire and an extension wire. Other modifications and improvements may be made with out departing from the scope of the invention.

What is claimed is:

1. A catheter exchange system which includes a guidewire and an extension wire with the proximal end of the guidewire being secured to the distal end of the extension wire, the catheter exchange system comprising:
    a) a guidewire which has a core member with a proximal end having male threads on the exterior thereof;
    b) an extension wire which has a tubular distal end with internal female threads adapted to threadably engage the male threads on the proximal end of the guidewire; and
    c) a removable connecting element comprising an elongated polymeric body having an inner lumen which has distal and proximal ends, the proximal end of the inner lumen being adapted to releasably secure by frictional engagement the distal end of an extension wire and the proximal end of the inner lumen being adapted to slidably receive the proximal end of a guidewire so as to allow the free rotation of the connecting element about the proximal end of the guidewire, the rotation of the connecting element causing the threaded engagement of the proximal end of the guidewire with the distal end of the extension wire.

2. The catheter exchange system of claim 1 wherein the connecting element has a slit which extends through the wall of the polymeric body along the length thereof.

3. A method of joining the proximal end of an elongated guiding member to the distal end of an extension wire to facilitate the exchange of a catheter, comprising:
    a) providing a guiding member having a proximal end with male threads on the exterior thereof;
    b) providing an extension wire having a tubular distal end with female threads on the interior thereof which match the male threads on the proximal end of the guiding member;
    c) providing a removable connecting element comprising an flexible elongated polymeric body having an inner lumen which has distal and proximal ends, with the proximal end of the inner lumen having the tubular distal end of the extension wire releasably secured by frictional engagement within the inner lumen thereof and the distal end of the inner lumen having the proximal end of the guiding member slidably disposed therein;

d) rotating the connecting element with respect to the proximal end of the guidewire to rotate the distal end of the extension wire secured within the connecting element to threadably engage the male threads on the guiding member with the female threads within the tubular distal end of the extension wire to thereby interconnect the proximal end of the guidewire with the distal end of the extension wire.

4. The method of claim 3 wherein the connecting element has a slit extending through the wall thereof along the length of the connecting element and the connecting element is separated from the connected guidewire or fixed-wire catheter and the extension wire, with the guidewire or fixed-wire catheter and the extension wire passing through the slit.

* * * * *